(12) United States Patent
Langlois et al.

(10) Patent No.: US 8,702,592 B2
(45) Date of Patent: Apr. 22, 2014

(54) SYSTEM AND METHOD FOR INHIBITING INJURY TO A PATIENT DURING LAPAROSCOPIC SURGERY

(76) Inventors: David Allan Langlois, Hamilton (CA); Lawrence Schembri, London (CA)

( * ) Notice: Subject to any disclaimer, the term of this patent is extended or adjusted under 35 U.S.C. 154(b) by 784 days.

(21) Appl. No.: 12/895,149

(22) Filed: Sep. 30, 2010

(65) Prior Publication Data

US 2012/0083652 A1    Apr. 5, 2012

(51) Int. Cl.
*A61B 1/00* (2006.01)
*A61B 1/04* (2006.01)
*A61B 1/06* (2006.01)

(52) U.S. Cl.
USPC .......................... 600/117; 600/118; 600/160

(58) Field of Classification Search
USPC .......... 600/104, 109, 117, 118, 160; 606/151, 606/174
See application file for complete search history.

(56) References Cited

U.S. PATENT DOCUMENTS

| | | | |
|---|---|---|---|
| 4,231,372 A | | 11/1980 | Newton |
| 4,742,815 A | * | 5/1988 | Ninan et al. ................. 600/118 |
| 5,098,426 A | | 3/1992 | Sklar et al. |
| 5,195,505 A | | 3/1993 | Josefsen |
| 5,199,419 A | | 4/1993 | Remiszewski et al. |
| 5,318,586 A | | 6/1994 | Ereren |
| 5,362,294 A | | 11/1994 | Seitzinger |
| 5,366,460 A | | 11/1994 | Eberbach |
| 5,379,754 A | * | 1/1995 | Tovey et al. ................... 600/109 |
| 5,381,788 A | | 1/1995 | Matula et al. |
| 5,383,477 A | | 1/1995 | DeMatteis |
| 5,397,331 A | | 3/1995 | Himpens et al. |
| 5,405,360 A | | 4/1995 | Tovey |
| 5,425,357 A | | 6/1995 | Moll et al. |
| 5,439,476 A | | 8/1995 | Frantzides |
| 5,465,711 A | | 11/1995 | Moll et al. |
| 5,503,320 A | * | 4/1996 | Webster et al. ............ 227/176.1 |
| 5,515,853 A | | 5/1996 | Smith et al. |
| 5,518,164 A | | 5/1996 | Hooven |

(Continued)

FOREIGN PATENT DOCUMENTS

| | | |
|---|---|---|
| EP | 0525791 | 2/1993 |
| EP | 2085045 | 8/2009 |

(Continued)

*Primary Examiner* — Philip R Smith
*Assistant Examiner* — William Chou
(74) *Attorney, Agent, or Firm* — Millman IP Inc.

(57) ABSTRACT

This group of inventions provides means and methods for preventing the damaging portions of surgical tools, such as laparoscopic devices, from adversely contacting tissues and organs that are not in the desired field of surgery. As such, the present disclosure pertains to any form of a warning or positioning device or methods, including those that are facilitated via software that are adapted and arranged for use in tracking portions of surgical instruments during laparoscopic surgery or other medical procedures. Such systems include those that are adapted and arranged to provide a warning to the surgeon or other medical personnel regarding the positional status of an instrument, and those that are adapted and arranged for disabling or attenuating the portions of those instruments that might be dangerous to a patient when a dangerous portion of the instrument is near or outside the desired, or denominated, field of surgery. Data relating to the position and orientation of the instrument and of the position of a safe zone within which the instrument can be kept safely is optionally (preferably) stored throughout a medical procedure for later playback for training purposes or for ensuring that a patient was not injured during a medical procedure.

30 Claims, 12 Drawing Sheets

(56) References Cited

U.S. PATENT DOCUMENTS

| | | |
|---|---|---|
| 5,554,101 A | 9/1996 | Matula et al. |
| 5,575,759 A | 11/1996 | Moll et al. |
| 5,803,902 A | 9/1998 | Sienkiewicz |
| 5,823,945 A | 10/1998 | Moll et al. |
| 5,865,728 A | 2/1999 | Moll et al. |
| 5,978,696 A | 11/1999 | Vomlehn et al. |
| 6,080,168 A | 6/2000 | Levin et al. |
| 6,099,518 A | 8/2000 | Adams et al. |
| 6,193,731 B1 | 2/2001 | Oppelt et al. |
| 6,246,898 B1 | 6/2001 | Vesely et al. |
| 6,258,113 B1 | 7/2001 | Adams |
| 6,321,106 B1 | 11/2001 | Lemelson |
| 6,332,089 B1 | 12/2001 | Acker et al. |
| 6,589,163 B2 * | 7/2003 | Aizawa et al. .............. 600/118 |
| 6,618,612 B1 | 9/2003 | Acker et al. |
| 6,638,292 B2 | 10/2003 | Adams et al. |
| 6,656,136 B1 | 12/2003 | Weng et al. |
| 6,768,496 B2 | 7/2004 | Bieger et al. |
| 6,796,940 B2 | 9/2004 | Bonadio et al. |
| 6,892,090 B2 | 5/2005 | Verard et al. |
| 6,926,706 B1 | 8/2005 | Sealfon |
| 6,926,709 B2 | 8/2005 | Bieger et al. |
| 6,973,202 B2 | 12/2005 | Mostafavi |
| 7,001,405 B2 | 2/2006 | Kieturakis et al. |
| 7,007,699 B2 | 3/2006 | Martinelli et al. |
| 7,057,148 B2 | 6/2006 | Wang |
| 7,072,704 B2 * | 7/2006 | Bucholz ..................... 600/407 |
| 7,112,072 B2 | 9/2006 | Korsunsky et al. |
| 7,154,157 B2 | 12/2006 | Bradski et al. |
| 7,214,236 B2 | 5/2007 | Kieturakis et al. |
| 7,217,276 B2 | 5/2007 | Henderson et al. |
| 7,311,661 B2 | 12/2007 | Heinrich |
| 7,313,430 B2 | 12/2007 | Urquhart et al. |
| 7,327,306 B2 | 2/2008 | Laroche |
| 7,332,642 B2 | 2/2008 | Liu |
| 7,333,642 B2 | 2/2008 | Green |
| 7,366,562 B2 | 4/2008 | Dukesherer et al. |
| 7,444,178 B2 | 10/2008 | Goldbach |
| 7,445,598 B2 | 11/2008 | Orban |
| 7,612,708 B2 | 11/2009 | Laroche |
| 7,660,623 B2 | 2/2010 | Hunter et al. |
| 8,473,026 B2 * | 6/2013 | Ferre et al. .................... 600/407 |
| 2003/0130576 A1 | 7/2003 | Seeley et al. |
| 2004/0054248 A1 | 3/2004 | Kimchy et al. |
| 2005/0119694 A1 | 6/2005 | Jacobs et al. |
| 2005/0287468 A1 | 12/2005 | Goodin |
| 2006/0258938 A1 | 11/2006 | Hoffman et al. |
| 2006/0293563 A1 * | 12/2006 | Banik et al. .................. 600/117 |
| 2007/0185506 A1 | 8/2007 | Jackson |
| 2007/0188606 A1 | 8/2007 | Atkinson et al. |
| 2007/0225550 A1 | 9/2007 | Gattani et al. |
| 2007/0285554 A1 | 12/2007 | Givon |
| 2008/0039715 A1 | 2/2008 | Wilson et al. |
| 2008/0065109 A1 | 3/2008 | Larkin |
| 2008/0091215 A1 | 4/2008 | Saleh |
| 2008/0120568 A1 | 5/2008 | Jian et al. |
| 2008/0146881 A1 | 6/2008 | Alimi et al. |
| 2009/0259123 A1 * | 10/2009 | Navab et al. .................. 600/424 |
| 2009/0267765 A1 | 10/2009 | Greene et al. |
| 2009/0277959 A1 | 11/2009 | Grimard |
| 2013/0211196 A1 * | 8/2013 | Belson et al. ................. 600/104 |

FOREIGN PATENT DOCUMENTS

| | | |
|---|---|---|
| EP | 2098180 | 9/2009 |
| FR | 2805731 | 1/2000 |
| WO | WO 2007/131561 | 11/2007 |
| WO | WO 2009/131561 | 10/2009 |

* cited by examiner

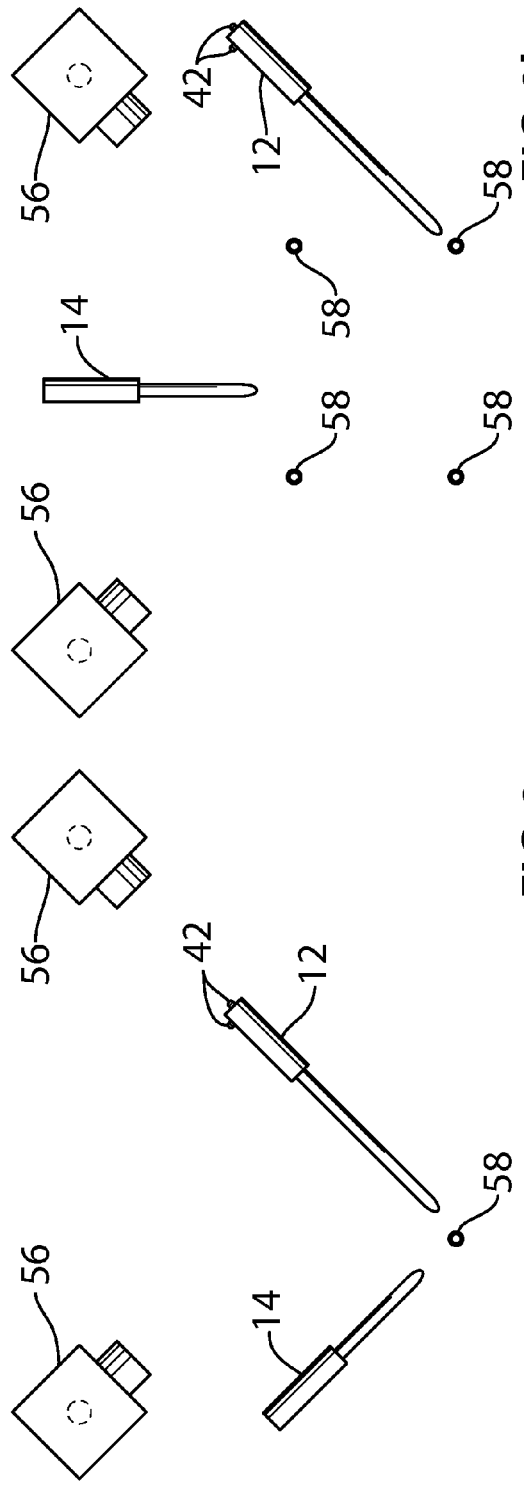
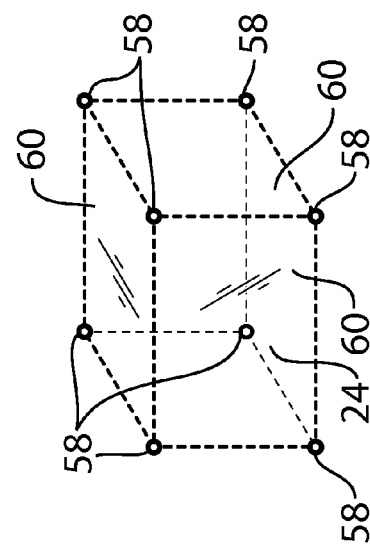
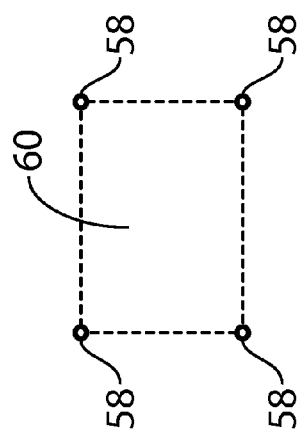
FIG. 2a
FIG. 2b
FIG. 2c
FIG. 2d

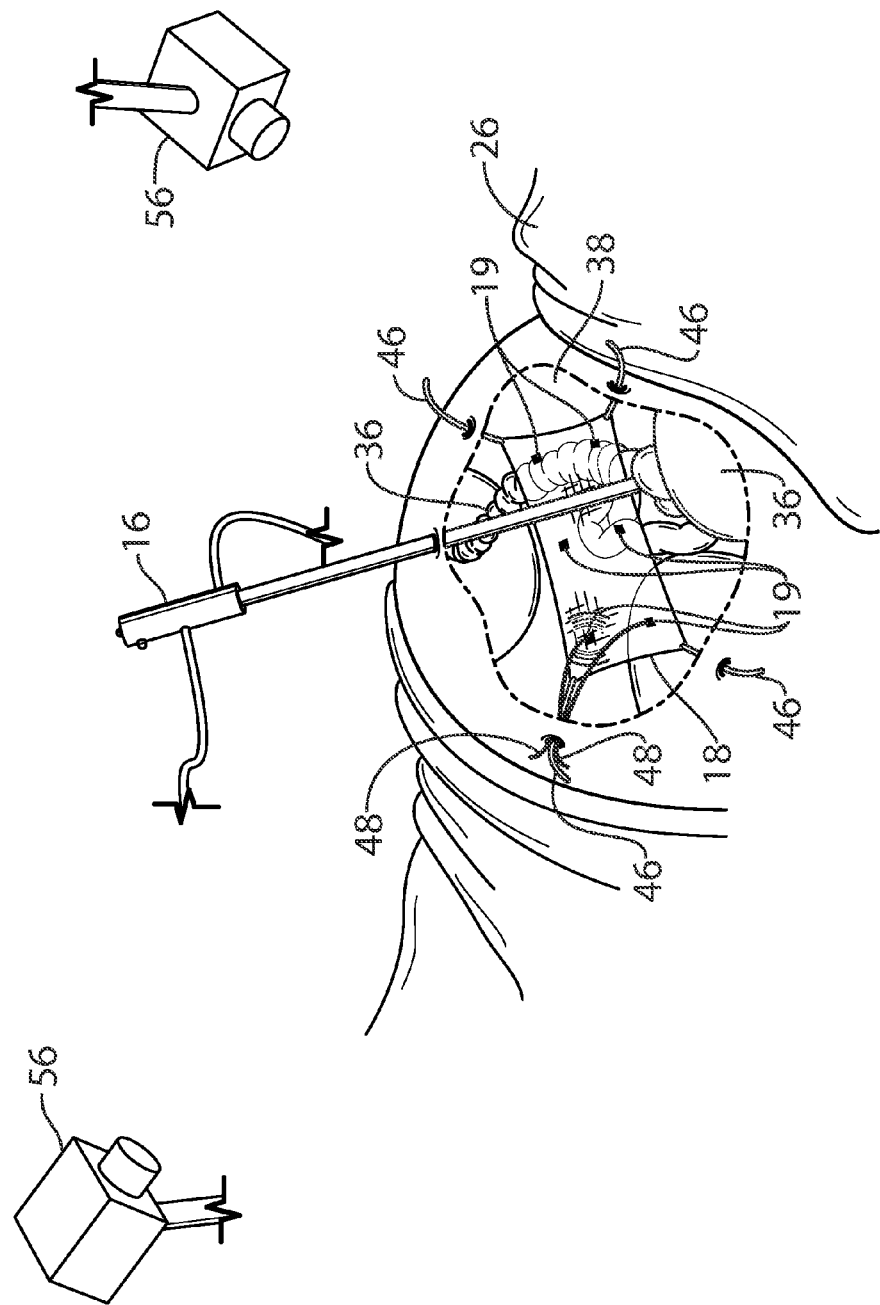

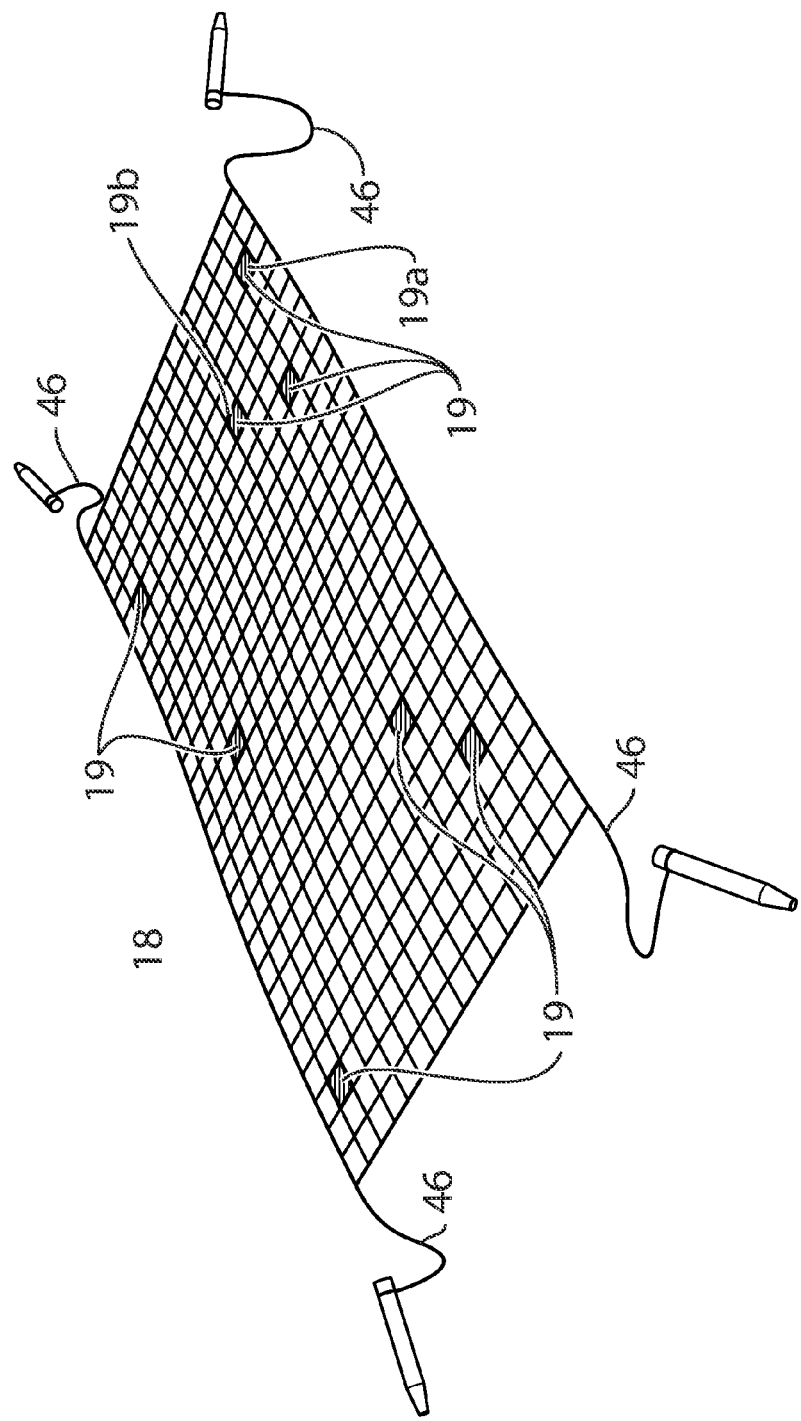

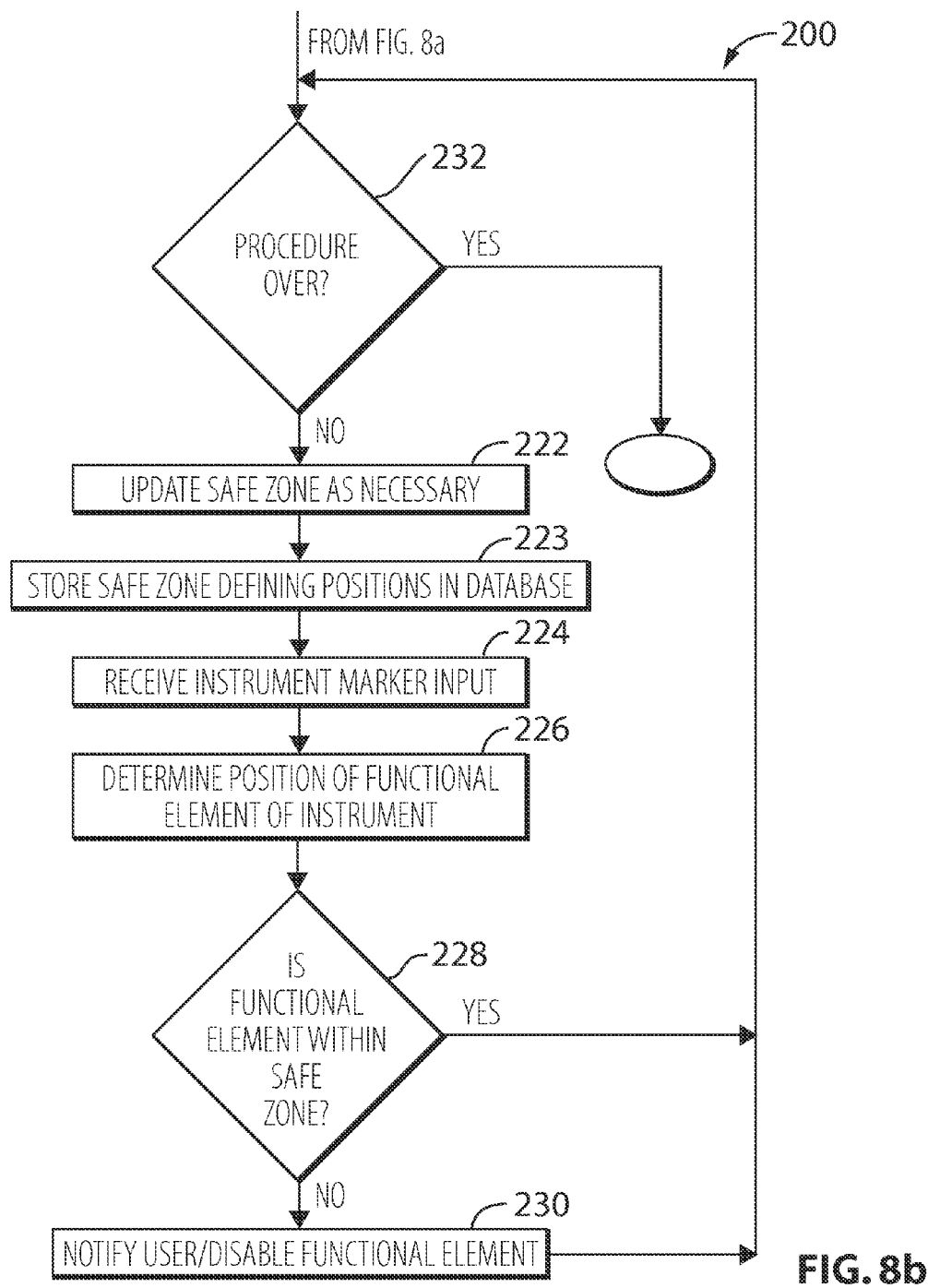

SYSTEM AND METHOD FOR INHIBITING INJURY TO A PATIENT DURING LAPAROSCOPIC SURGERY

FIELD OF THE INVENTION

The present invention relates to systems for reducing accidental injury to patients during surgery and more particularly during laparoscopic surgery.

BACKGROUND OF THE INVENTION

Compared with conventional surgery, laparoscopic surgery is an excellent means for achieving significant reductions in surgery-related morbidity. These reductions are achieved, however, only if the procedure is performed completely and without effective errors. Unfortunately, error-free laparoscopic surgeries are not the rule. Indeed, intra-operative and post-operative complications are all too common with laparoscopic surgery procedures. Because of this, there is a need to improve patient safety during laparoscopic surgery so that the benefits derived from such procedures are achieved while the drawbacks are reduced or eliminated.

One of the most profound drawbacks of laparoscopic surgery is the occurrence of unintentional or inadvertent injuries to patient tissue structures adjacent to or sometimes, distant from the intended surgical site or field. In the pelvic cavity, for example, bowels, ureters, large organs and blood vessels can be injured either directly from the heat or sharpness of the laparoscopic instruments, or burned indirectly through the conduction of heat through nearby tissues. Typically, such injuries are not appreciated at the time of surgery because the specific injury sites are hidden by blood or other patient tissues. As another disadvantage attendant to such iatrogenic injuries, the response to the unintended injury manifested by the patient is often a delayed one. This delayed response can be traumatic as well as tragic, and can sometimes result in one or more further surgeries, which would otherwise be unnecessary.

The implications from both a medical perspective as well as a medico-legal perspective are enormous. Obviously, such injuries are negative events and therefore best avoided. The present invention is therefore directed to reducing the occurrence and severity of these negative events.

SUMMARY OF THE INVENTION

In one aspect, the invention defines or denominates a surgical field as a three-dimensional space in which the operative portions of laparoscopic instruments, those portions which are capable of causing harm to the patient or medical personnel, are permitted to function. In some embodiments, the hazardous or dangerous function of the instruments can be automatically attenuated or eliminated outside of this denominated space. The operative portions of a laparoscopic instrument or appliance include those that can potentially cause damage if they contact a patient's tissues in an unintended manner. Examples of such potentially damaging portions include hot wires, electrically charged wires, blades, scissors and shears, sharp points or surfaces. Thus, the operative portions can include those that are adapted and arranged to do one or more of cut, cauterize, ablate, seal, fuse, skewer or clamp.

In another significant aspect, in order to track and monitor the relative positions and orientations of the instruments with respect to the protected space, and in order to track a probe used to assist in defining the protected space (ie. a safe zone) the present invention employs one or more of software, optics, high speed digital imaging, such as visible spectrum or infrared (IR) imaging, 2D or 3D ultra sound, MRI and CAT scan images, visible spectrum or infrared (IR) imaging, photography, electromagnetic sensing, radio frequency (RF) sensing as well as one or more sensors to enable the surgeon, operating room and other medical personnel, including remote medical personnel, to be apprised of the precise positional status of the laparoscopic instruments being used.

Positional status refers to the relative position of the operative and non-operative portions of the various laparoscopic appliances and tools being used with respect to various portions of the patient's body, or with respect to the denominated surgical field, or with respect to one or more sensors placed inside or outside the patient's body.

A positive positional status refers to circumstances where the operative portions of the laparoscopic instruments are within the denominated boundaries of the surgical field. A neutral positional status refers to circumstances where the operative portions of the laparoscopic instruments are in the denominated surgical field but near at least one boundary. A negative positional status refers to circumstances where the operative portions of the laparoscopic instruments are outside of the denominated surgical field, or within a predetermined distance of a sensor.

Positional status is determined with respect to a three-dimensional surgical field having defined boundaries, or with respect to one or more sensors placed in proximity to vulnerable tissues. In accordance with certain aspects of the invention, those boundaries can be defined in a number of different ways and combinations thereof. For example, in some embodiments, proximity to one or more sensors placed on a vulnerable organ or tissue defines the boundaries of the protected space or denominated field. In other embodiments of the invention, the boundaries of the field can be determined with respect to distance from an object, such as a net used for sequestering the bowel, and the like. Thus, definition of the various boundaries makes it possible to determine the relative positions of various portions of laparoscopic instruments with respect to the denominated surgical field, and with respect to vulnerable tissues and organs, as well as with respect to various medical personnel.

Thus, in accordance with an embodiment of the invention, the three-dimensional spatial boundaries of a surgical field can be determined, or denominated, in a number of different ways. The present means and methods thus denominate the shape and volume of a three-dimensional space, and also track the position of portions of various instruments with respect to that space. By doing so, the likelihood of inadvertent damage is decreased. This is further enhanced by other aspects of the invention.

For example, each laparoscopic instrument being used in a particular procedure can have a range of statuses. Each of these statuses can be determined by the instrument's relative position in the denominated field, for example, by means of distance sensors, magnetic sensors, heat sensors, proximity sensors, 2D or 3D imaging technologies (Ultra-sound, MRI, etc.) and the like.

Thus, a system of the present invention "knows" where inside the body the operative portions of the laparoscopic instruments are located at all times. The sensors therefore aid the surgeon in staying away from vulnerable tissues and areas within the patient's body. Moreover, the instruments can be in operative communication, programmed or coded to shut off in the event that a dangerous structure is within the radius of a direct injury or a thermal burn, for instance. In an embodiment the invention reduces morbidity by providing the surgeon and other medical personnel with a "denominated surgical field" or "protected space" within which to perform the indicated procedure while reducing the risk of damage to other organs which, in essence, are provided with a kind of "force field" around them. Thus, in one aspect, the means and methods of the invention function to sequester vulnerable portions of the patient's body.

When the borders or limits of the denominated field are breached are approached, the system provides also for warnings to be given, such as a buzz or handle vibration in the laparoscopic tool being used. A system in accordance with an embodiment of the invention can thus be adapted and arranged such that the energized or sharp portions of the appliance are operational only within the boundaries determined by the sensor-enabled laparoscopic field, that is, the denominated field. As an example, in some embodiments, the means and methods of the invention can be adapted and arranged such that the sharp edges of the appliance are automatically withdrawn into one or more sheaths provided as part of the laparoscopic appliance.

In other embodiments of the invention, the means and methods of the invention can be effected by way of software that controls the various energy inputs to the laparoscopic instruments being used, thus preventing the unwanted cutting, avulsing, cauterizing, ablating, or severing of a patient's tissues and organs.

As yet another advantage, the means and methods of the present invention can also be adapted and arranged as teaching tools for providing virtually instantaneous feedback to surgeons and other medical personnel regarding their abilities and techniques in laparoscopic surgery. Various feedback loops and sensitivities of the invention can be adjusted to provide tailored instruction with respect to instructional or experimental surgeries on animals or models.

In some embodiments, all points, co-ordinates, positions and movements of instruments, body, organs and tissues can be recorded and stored for later playback if necessary. The playback can be provided in any of the following formats: audio, graphs, 2D graphic, and 3D graphic, or in any combination thereof.

In another aspect, the invention is directed to a surgical system for use on a body of a patient, wherein the system permits the user to determine the positions of a plurality of points on internal body portions of the patient surrounding a surgical field, wherein the points are used by a controller to determine a safe zone in which a functional element on a surgical instrument can be positioned without causing injury to the patient. The positions of the points may be monitored by the controller in real time so that if, after the safe zone is determined initially by the controller, the internal body portions of the patient move, the controller updates the data relating to the safe zone in real time. The system uses a sensor net that is positioned in the surgical field to assist in determining the points that define the safe zone both initially and in real time during a medical procedure.

In another aspect, the invention is directed to a method of using a surgical system on a body of a patient. The method is used to determine the positions of a plurality of points on internal body portions of the patient surrounding a surgical field, in order to determine a safe zone in which a functional element on a surgical instrument can be positioned without causing injury to the patient. The positions of the points may be updated in real time during a medical procedure so that if the internal body portions of the patient move after the safe zone is determined initially, the data relating to the position of the safe zone can be updated in real time. The method incorporates the use of a sensor net that is positioned in the surgical field to assist in the determining of the points that define the safe zone both initially and in real time during a medical procedure.

BRIEF DESCRIPTION OF THE DRAWINGS

FIGS. 2a-2d illustrate the surgical system shown in FIG. 1 being used to determine a safe zone within the patient in which a surgical instrument can be maneuvered without causing injury to the patient;

FIG. 3 is a perspective view of an optional net that can be included with the system shown in FIG. 1;

FIG. 5 is a magnified perspective view of the net shown in FIG. 3

FIGS. 8a and 8b are a flow diagram of the programming for a controller in the surgical system shown in FIG. 1.

DETAILED DESCRIPTION OF THE INVENTION

Figure 1:
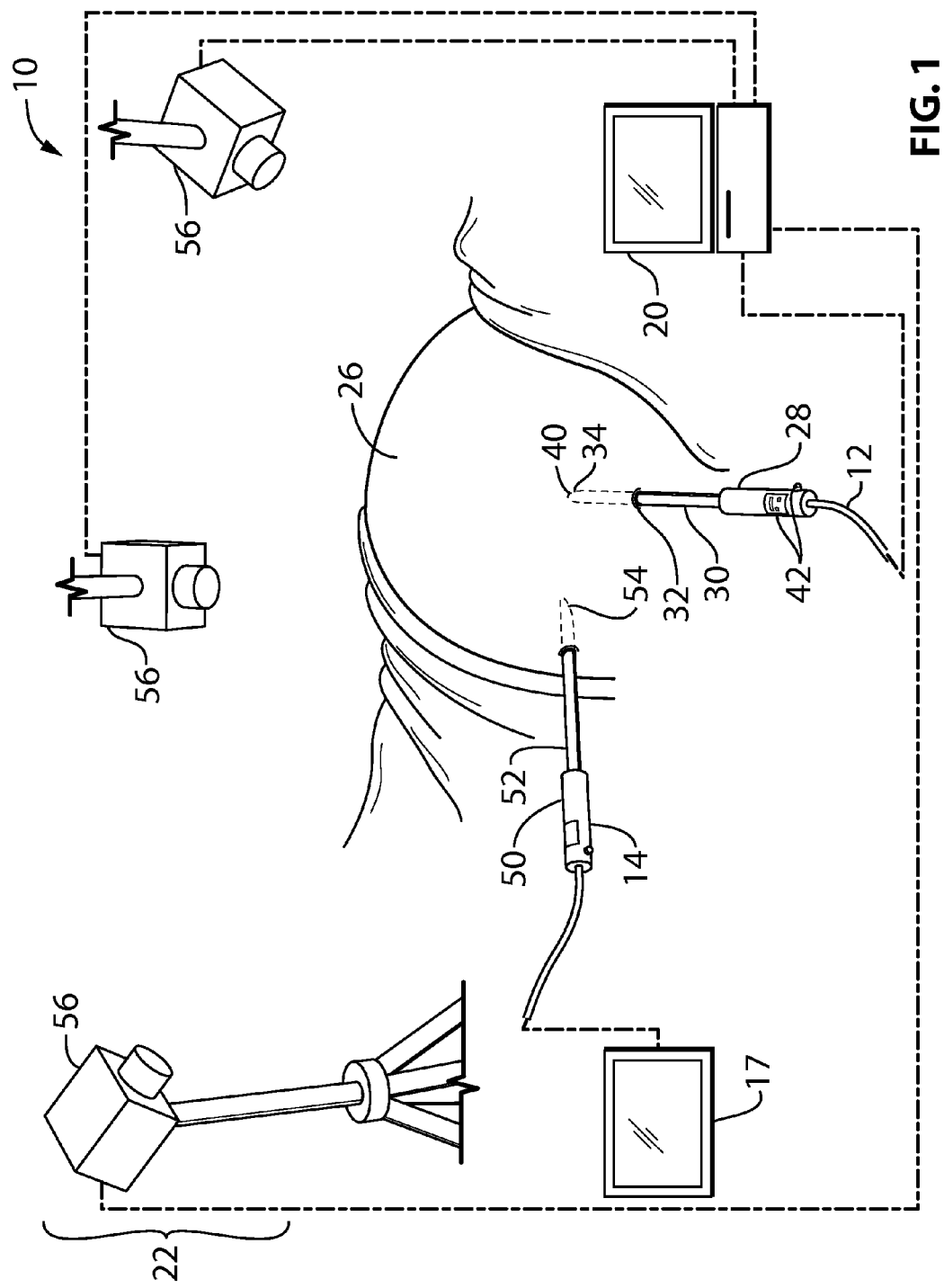
FIG. 1 is a perspective view of a surgical system for use on the body of a patient in accordance with an embodiment of the present invention.

Reference is made to FIG. 1 which shows a surgical system 10 for use on a body of a patient in accordance with an embodiment of the invention. The surgical system 10 includes a probe 12, a laparoscope 14, a surgical instrument 16 (FIG. 3), a display 17, netting 18 (FIG. 3) with a plurality of safe zone definition sensors 19 on it, a controller 20 and a tracking system 22, which in the embodiment shown is a camera system. The surgical system 10 is configured to reduce the incidence of injuries to patients during laparoscopic surgery.

Figure 2E:
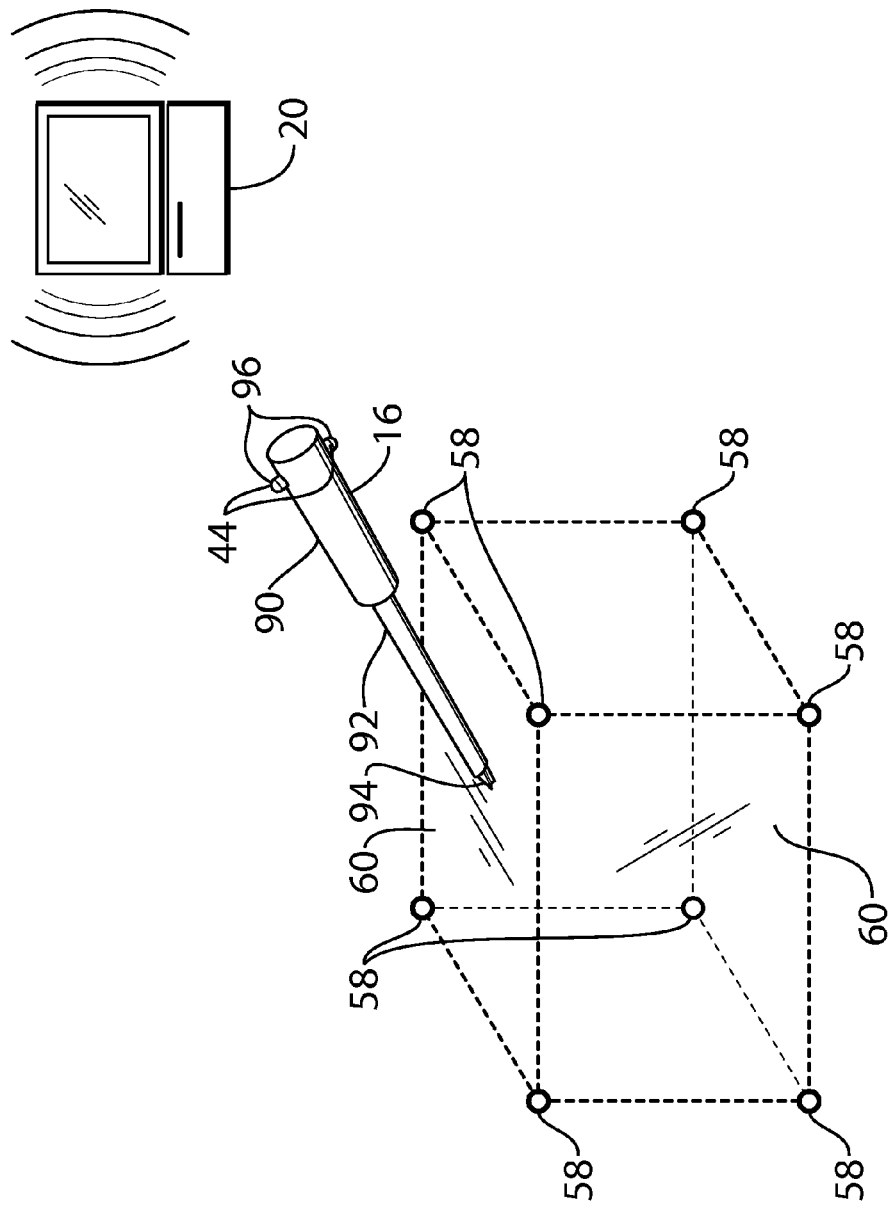
FIG. 2e is a perspective view of a surgical instrument being used during a surgical procedure.

The system 10 is initially used to determine a safe zone 24 (FIG. 2e) within the patient shown at 26 (only a portion of the patient 26 is shown in FIG. 1) in which the surgical instrument 16 can be maneuvered without causing injury to the patient 26. The determination of the safe zone 24 involves the probe 12, the laparoscope 14 in particular. The probe 12 includes a probe body 28 and an interior portion 30 connected to the probe body 28. The interior portion 30 is configured to be at least partially inserted into the body of the patient 26 through one of a plurality of apertures 32 made in the body of the patient 26. The particular aperture 32 through which the probe 12 is inserted is shown at 32a. The interior portion 30 is therefore made from a material that will not cause harm to the patient, such as, for example, a suitable stainless steel. The probe body 28 is configured to be outside the body of the patient 26 during use.

The probe 12 further includes a probing portion 34 on the interior portion 30. The probing portion 34 is a portion of the interior portion 30 and is used to identify the positions of points on the internal body portions shown at 36 (FIG. 3) of the patient 26 that are in the surgical field (ie. that are in the vicinity of the particular site in the patient 26 that requires surgery). The surgical field is shown in FIG. 3 at 38. Referring to FIG. 2a, the probing portion 34 may be at a tip 40 of the interior portion 30. The probing portion 34 may have one or more selected properties which may be different from the rest of the interior portion 30 so that other portions of the interior portion 30 cannot be mistaken by the system 10 as being the probing portion 34. For example, the probing portion 34 may be configured to be magnetic. Alternatively, the probing portion 34 may be configured to be electrically conductive. Alternatively, the probing portion 34 may be heated to a selected temperature. Alternatively, the probing portion 34 may be configured to emit signals at a selected frequency and strength. Alternatively, the probing portion 34 may simply be of the same material as the rest of the interior portion 30, and may simply be conveniently shaped so as to permit easy pointing at an object (eg. an internal body portion 36).

During use of the probe 12 it is desired for the controller 20 to be able to determine the position of the probing portion 34 at selected times. To this end, a probe marker 42 is provided on the probe body 28. The probe marker 42 is, during use, viewed by the camera system 22 and is used by the controller 20 to identify the probe 12 (ie. to distinguish the probe 12 over other objects, such as the instrument 16). Additionally or alternatively, the probe marker 42 is configured to provide sufficient information to the controller 20 for the controller 20 to be able to determine the position and orientation of the probe marker 34. By determining the position and orientation of the probe marker 34, the controller 20 can determine the position and orientation of the probe 12 itself and therefore can determine the position of the probing portion 34. Determining the position of the probing portion 34 is used by the controller 12 in determining where the internal body portions 36 of the patient 26 are, which is then used by the controller 20 to determine the safe zone 24.

Figure 6B:
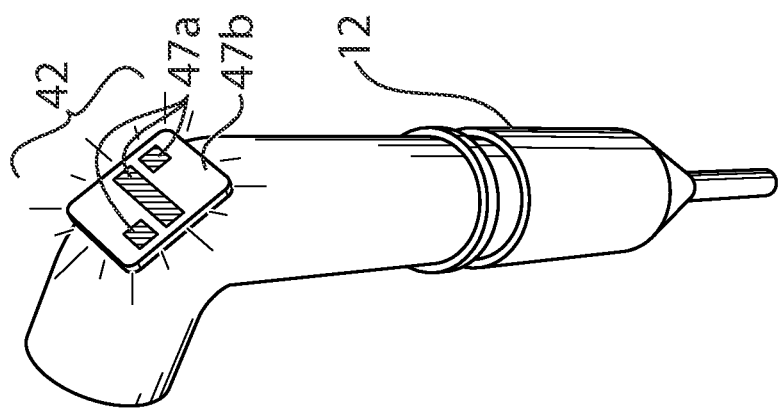
FIGS. 6a-6d are examples of markers that can be included on a surgical instrument shown in FIG. 1 to permit tracking of the surgical instrument by a camera system.
Figure 6A:
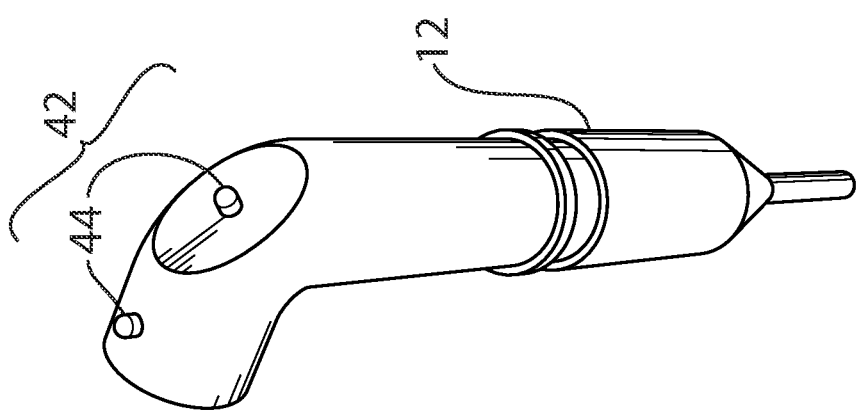
Figure 6D:
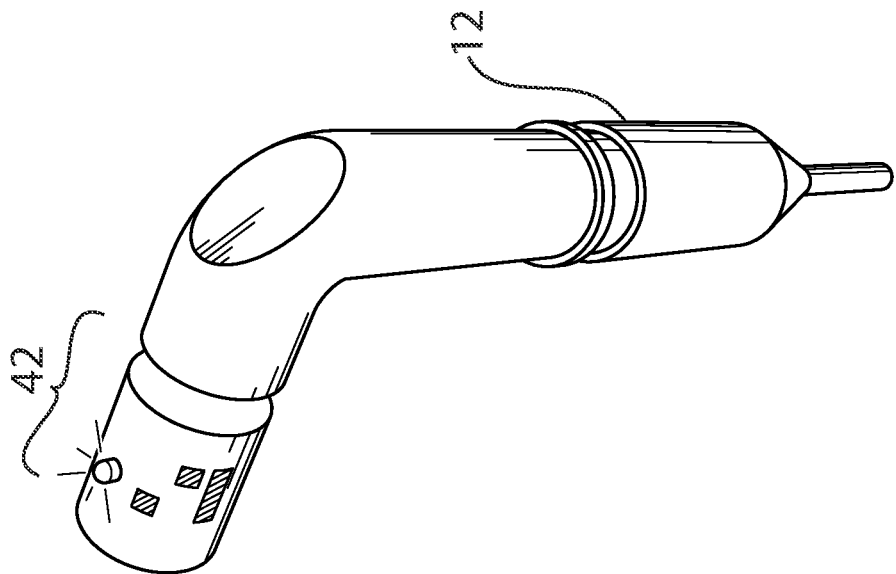

As shown in FIG. 6a the probe marker 42 may, for example, be made up of a plurality of LEDs 44 on the probe 12. Some aspect of the LEDs 44 is unique so as to facilitate detection of the probe marker 42 in the images sent by the camera system 22 to the controller 20 and optionally to distinguish the probe marker 42 from an analogous marker on the surgical instrument 16. For example, the arrangement of the LEDs 44 on the probe body 28 may be distinguishable by the controller 20 to detect the probe marker 42 and optionally to identify it as the probe marker 42 as opposed to the aforementioned marker on the surgical instrument. Alternatively or additionally, the LEDs 44 may be configured to emit light at a particular wavelength or combination of wavelengths of light.

The LEDs 44 may be configured to emit light at a non-visible wavelength (eg. infrared) so as to not distract the user of the probe 12 (eg. the surgeon) during use.

Figure 6C:
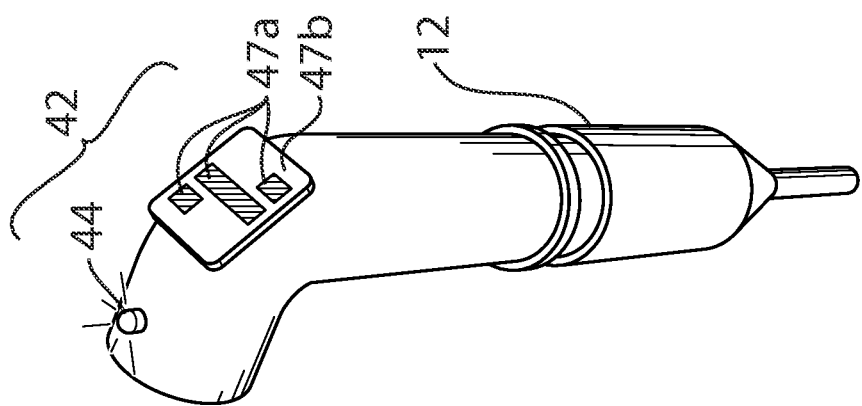

As an alternative to LEDs, the probe marker 42 may be made up of any suitable means for identifying the probe 12 and for identifying the position and orientation of the probe 12. For example, the probe marker 42 may include one or more symbols 47a (eg. polygons) on a suitable background 47b as shown in FIG. 6b. The colour of the symbols 47a and the colour of the background 47b may be selected to be of sufficient contrast to facilitate locating the symbols on the background, and may be selected to be sufficiently unique so as to permit the controller 20 to detect the probe marker 42 in the images provided by the camera system 22. Alternatively, as shown in FIG. 6c, a combination of LEDs 44 and symbols 47a and a background 47b may be provided. As shown in FIG. 4d, the probe marker 42 may be removable from the probe body 28. For example, the marker 42 may be provided on a sleeve.

The netting 18 may have several purposes. For example, the netting 18 may be positionable to restrain at least some of the internal body portions 36 in the surgical field 38 from obstructing the surgical instrument 16 when the surgical instrument 16 is being used in the surgical field 38. Alternatively, the netting 18 may simply be provided to conform to the shape of at least some of the internal body portions 36 in the surgical field 38. The netting 18 may be provided with any suitable means for restraining the internal body portions 36. For example, the netting 18 may be provided with a plurality of hold down members 46 which extend out of the body of the patient 26 and which may be attached to suitable attachment points on a support frame (not shown). Alternatively, the netting 18 may be provided with one or more hold down members that connect to other points within the body of the patient 26. Alternatively, the netting 18 may be provided with a grippy, elastic peripheral edge permitting the netting 18 to be mounted over internal body portions 36 and to hold on to the body portions 36 themselves. The netting 18 may be made up of one or more individual nets each of which is affixed to internal body portions 36 around the surgical field 38.

The plurality of safe zone definition sensors 19 on the netting 18 are configured to communicate with the controller 20 and to cooperate with the probe 12 to establish the positions of points on at least some internal body portions 36 in the surgical field 38 to assist in the determination of the safe zone 24 by the controller 20. The safe zone definition sensors 19 may be any suitable type of sensors, such as, for example, electromagnetic (EM) sensors, magnetic sensors, heat sensors, radio frequency (RF) sensors, proximity sensors, GPS, Hall Effect sensors and any other suitable type of sensor. Each safe zone definition sensor 19 is configured to detect when the probing portion 34 is at a selected proximity to it.

In an exemplary embodiment, each safe zone definition sensor 19 is configured to detect when it is contacted by the probing portion 34. For example, the sensor 19 may be configured to detect self-movement, which would take place when contacted by the probing portion 34. Alternatively or additionally the sensor 19 may determine contact by the probing portion 34 by some other means. For example, contact with the probing portion 34 may close an electrical circuit through the sensor 19, which could be used to send a signal to the controller 20 that contact is made with the probe 12.

Each sensor 19 may include an accelerometer that is capable of detecting self-movement in three dimensions. When detecting self-movement, the sensor 19 is configured to communicate the amount of self-movement to the controller 20 so that the controller 20 can update the position of the sensor 19 in real time. Because the position of the sensors 19 indicates the position of the internal body portions 36 of the patient 26, the controller 20 can thus determine if the internal body portions 36 move during surgery, and can use this information to continuously determine a new safe zone 24 (FIG. 2e) in real time during surgery.

The sensors 19 may communicate with the controller 20 via any suitable means. For example, an electrical conduit 48 (FIG. 3) may extend from the sensors 19 out of the body of the patient 26 to the controller 20.

The laparoscope 14 includes a laparoscope body 50 and an interior portion 52 connected to the laparoscope body 50. The interior portion 52 is configured to be at least partially inserted into the body of the patient 26 through one of the apertures 32. The particular aperture 32 through which the probe 12 is inserted is shown at 32b. The interior portion 52 is therefore made from a material that will not cause harm to the patient, such as, for example, a suitable stainless steel. The laparoscope body 50 is configured to be outside the body of the patient 26 during use.

The interior portion 52 includes an image receiving element 54. During use, the image receiving element 54 is positionable in the surgical field 38 in the body of the patient 26 to receive images of the probing portion 34 when the image receiving element 54 is in the surgical field 38. The image receiving element 54 may be a lens, for example. The laparoscope 14 is configured by any suitable means to transmit received images to the display 17. For example, the laparoscope 14 may include an image sensor (not shown), which may be, for example, a CCD sensor or a CMOS sensor, that is positioned to receive images from the image receiving element 54. The laparoscope 14 is configured to transmit the images of the probing portion 34 to the display 17 (optionally via a controller such as the controller 20).

The surgical instrument 16 includes an instrument body 90 and an interior portion 92 connected to the instrument body 90. The interior portion 92 is configured to be at least partially inserted into the body of the patient 26 during use. The instrument body is configured to be outside the body of the patient during use. The interior portion 92 includes a functional element 94, which is an element that is configured to perform a particular function on the patient. For example, the functional element 94 may be a cutting blade, a scissors mechanism or for example a heating element to cauterize. As will be understood, the functional element 94 may cause unintended injury to the patient 26 if it is accidentally brought into contact with the internal body portions 36 of the patient 26 surrounding the surgical field 38.

During use of the surgical instrument 16 it is desired for the controller 20 to be able to determine the position of the functional element 94 substantially continuously. To this end, an instrument marker 96 is provided on the instrument body 90. The instrument marker 96 is, during use, viewed by the camera system 22 and may be used by the controller 20 to identify the surgical instrument 16 (ie. to distinguish the surgical instrument 16 over other objects, such as the probe 12). Additionally or alternatively, the instrument marker 96 is configured to provide sufficient information to the controller 20 for the controller 20 to be able to determine the position and orientation of the instrument 16. By determining the position and orientation of the instrument marker 96, the controller 20 can determine the position and orientation of the surgical instrument 16 itself and therefore can determine the position of the functional element 94. Determining the position of the functional element 94 is used by the controller 12 in determining whether the functional element 94 is within the safe zone 24.

Figure 4B:
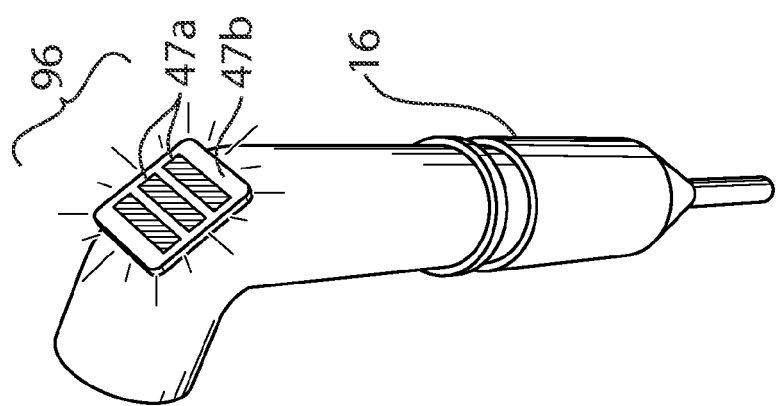
FIGS. 4a-4d are examples of markers that can be included on a probe shown in FIG. 1 to permit tracking of the probe by a camera system.
Figure 4A:
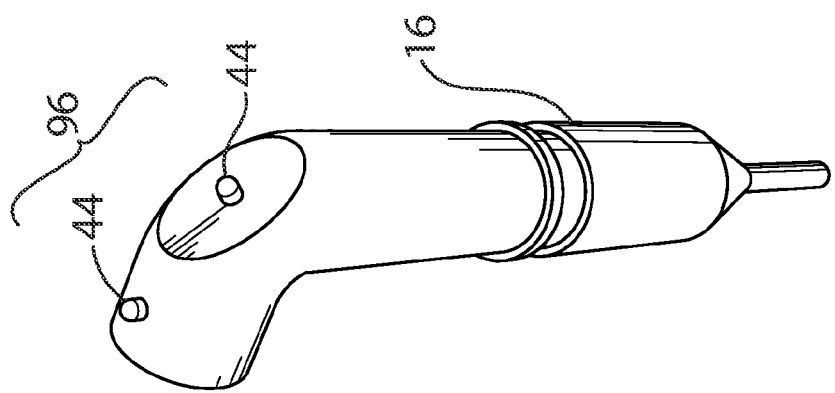
Figure 4C:
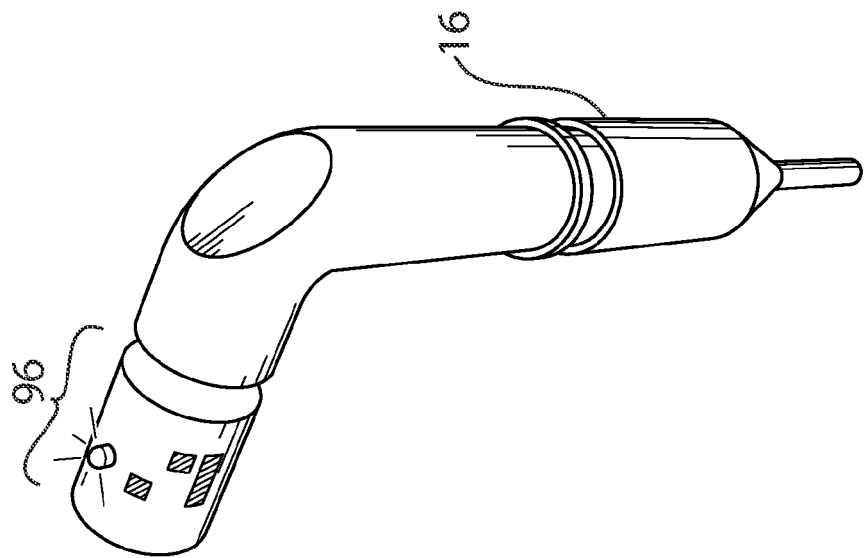
Figure 4D:
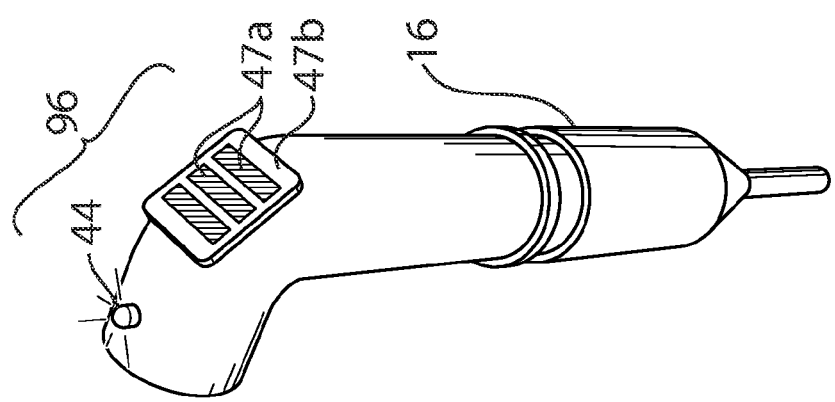

Some examples of instrument markers 96 are shown in FIGS. 4a, 4b, 4c and 4d. The instrument marker 96 may includes LEDs 44 (FIG. 4a), one or more symbols 47a (eg. polygons) on a suitable background 47b (FIG. 4b), or a combination of the two (FIG. 4c). The instrument marker 96 may be removable from the instrument body 90 as shown in FIG. 4d. For example it may be provided on a sleeve.

The camera system 22 includes at least one camera 56 and preferably includes a plurality of cameras 56 mounted around the surgical theatre. The cameras 56 are positioned at selected positions to reduce the likelihood of obstruction of their view of the probe marker 42 and the instrument marker 96. The cameras 56 receive images of the probe marker 42 and transmit the images to the controller 20. The controller 20 is programmed to locate the probe marker 42 in the images and to determine by any suitable means, the position and orientation of the probe 12 and therefore the position of the probing portion 34. This may be achieved by comparing the images from two or more cameras 56 and using triangulation. Alternatively, a stereoscopic camera 56 may be used, so as to provide three-dimensional position information through images sent to the controller 20 without using multiple cameras. Alternatively, a single non-stereoscopic camera 56 may be used which sends a non-stereoscopic image to the controller 20. The controller 20 can determine easily the position of the marker 42 in the two dimensional plane of the image easily and the depth of the probe marker 42 (ie. its distance from the camera along a third dimensional axis perpendicular to the plane of the image) may be determined based on the apparent size of the marker 42 in the image.

Providing two or more cameras 56 may be advantageous to reduce the likelihood of the surgeon's hands or body from preventing the camera system 22 from obtaining an unobstructed view of the probe marker 42. In an embodiment where at least two cameras 56 are required to have an unobstructed view of the marker 42, the camera system 22 preferably includes 3 or more cameras 56.

Instead of incorporating cameras, the tracking system 22 could alternatively incorporate other types of tracking system sensor that is configured to sense the position of the probe marker and the instrument marker. For example, the tracking system could incorporate one or more of the following exemplary techniques to sense the position of the instrument 16 and of the probe 12: 2D or 3D ultra sound, MRI and CAT scan images, electromagnetic sensing, radio frequency (RF) sensing. Regardless of the technique used, and the technology used, whatever is on the probe and on the instrument that is detected by the tracking system may be considered a probe marker and an instrument marker respectively.

Figure 8A:
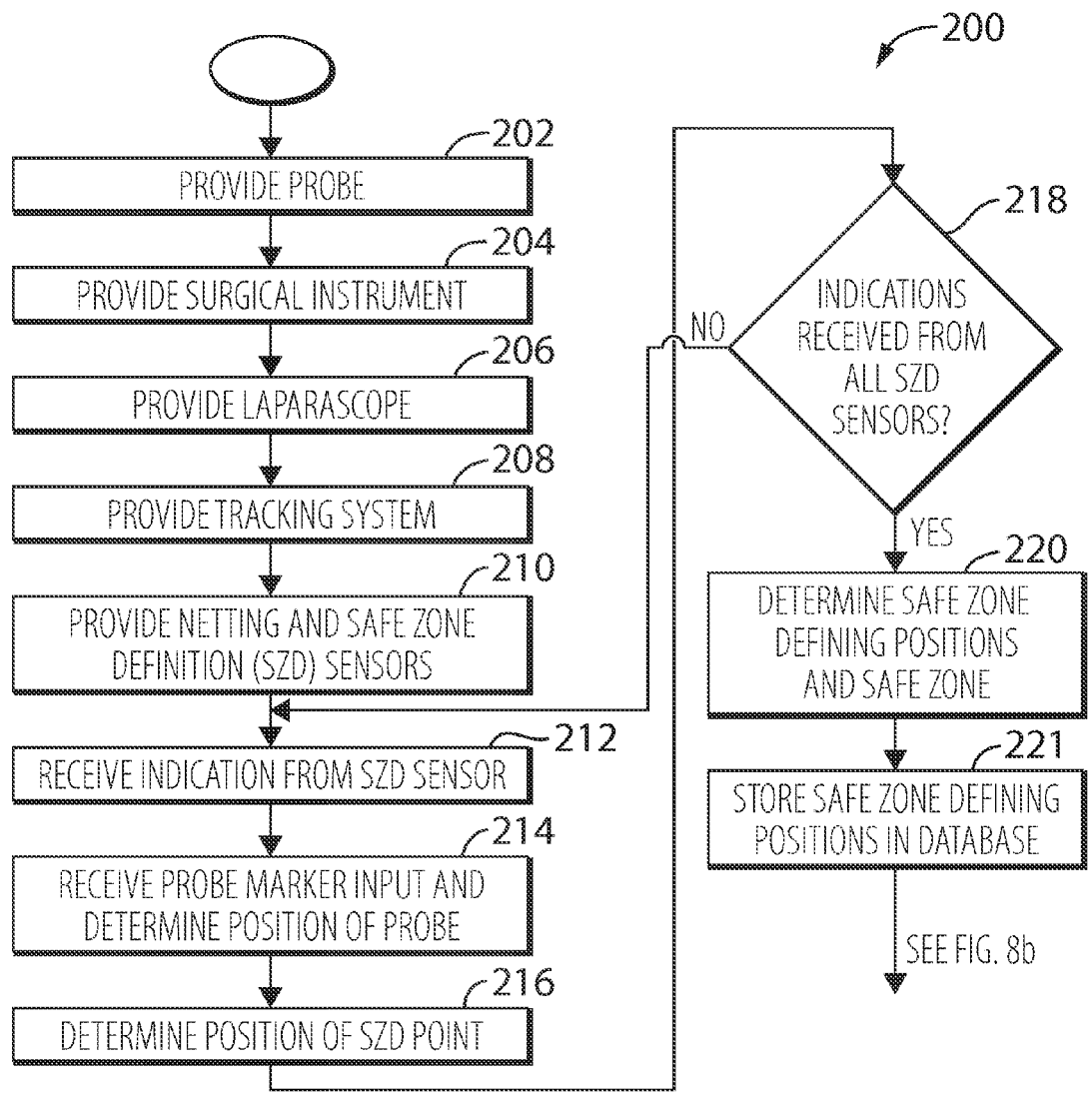

The operation of determining the safe zone 24 is as follows, with reference to FIGS. 1-6 and with reference to the flow diagram 200 shown in FIGS. 8a and 8b. Initially, a probe, a surgical instrument, a laparoscope, a tracking system, and netting with the sensors 19 therein are provided in steps 202, 204, 206, 208 and 210 (FIG. 8a). Then a plurality of points 58 on internal body portions 36 that surround the surgical field 38 are determined. To do this, the user creates the apertures 32. The user inserts the netting 18 with the sensors 19 thereon into the surgical field 38 through one of the apertures 32 and affixes the netting 18 as desired. The user inserts the laparoscope 14 into the surgical field 38. The user inserts the probe 12 into the surgical field 38. The camera system 22 receives images of the probe marker 42 and transmits the images to the controller 20 (the images thus constitute probe marker input). The user can see the probing portion 34 of the probe 12 on the display 17 via the transmission of images from the laparoscope 14 to the display 17. Using the images from the laparoscope 14 the user guides the probe 12 so that the probing portion 34 contacts a first of the safe zone identification sensors shown at 19a. When the first sensor 19a senses contact with the probing portion 34, the first sensor 19a indicates the occurrence of the contact to the controller 20 (step 212). In this particular example, the first point 58a on the internal body portions 36 is substantially immediately adjacent the probing portion 34, since they are separated only by the sensor 19a, which may be thin. When the controller 20 receives the indication from the first sensor 19a that contact was made, the controller 20 determines the position of the probing portion 34 of the probe 12 (step 214) based on the one or more images that were received from the camera system 22 at the time that the indication of contact from the sensor 19a was sent. The indication of the contact with the first sensor 19a, in combination with the one or more images from the camera system 22 may be considered input indicating the position of a first point 58a on the internal body portion 36. The controller 20 may use any suitable method for determining the position of the probing portion 34. The controller 20 uses the one or more images to determine the position and orientation of the probe marker 42, and thus the probe 12. The method used for this determination depends on whether the camera system 22 provides a single non-stereoscopic image, a plurality of non-stereoscopic images, or one or more stereoscopic images. It will be understood by one skilled in the art however, that many suitable algorithms exist for the determination of the position and orientation of an object using one or more images.

Once the controller 20 has determined the position and orientation of the probe 12, the controller 20 can then determine the position of the probing portion 34 based on the distance between a selected portion of the probe marker 42 and the probing portion 34 (which is a known value that is stored in the controller's memory). Using the position of the probing portion 34, the controller 20 can determine the position of the safe zone definition sensor 19a, and thus the position of point 58a (step 216). In this example, because the sensor 19a is substantially immediately adjacent the probing portion 34 and is thin, the determined position of the point 58a on the internal body portions 36 may be considered to be the same as the position of the probing portion 34. Once the position of the point 58a on the internal body portions 36 is determined, the controller 20 records it for use in determining the safe zone 24. After contacting the first sensor 19a, the user guides the probe 12 using the laparoscope 14 and display 17 so that the probing portion 34 contacts a second sensor 19b for the purpose of having the controller 20 determine the position of a second point 58b on the internal body portions 36. The user continues to go from sensor 19 to sensor 19 until all the sensors 19 have been contacted. In the flow diagram 200 this is shown by the controller 20 checking at step 218 if indications have been received from all the sensors 19 and sending program control back to prior to step 212 if the answer to the check step 218 is 'no'.

While one particular sensor 19 was referred to in this example as the first sensor 19a, it will be understood that any of the sensors 19 could have been referred to as the first sensor 19a, and any of the sensors 19 could have been referred to as sensor 19b, and so on.

Once the positions of the points 58 corresponding to the positions of the sensors 19 have been identified, (ie. the answer to check step 218 is 'yes') the controller 20 determines the safe zone 24 based on the points 58 (step 220). The points 58 may thus be referred to as safe zone defining points. The safe zone 24 may be determined by generating a plurality of virtual surfaces shown at 60 in FIG. 2d between the points 58. The controller 20 may generate the virtual surfaces 60 between groups of points 58, as shown in FIG. 2d. The surfaces 60 may, for example, be quadrilateral surfaces between groups of 4 points 58, or may be triangular surfaces between groups of 3 points 58, or may be surfaces having some other number of sides between correspondingly sized groups of points 58. The virtual surfaces 60 define the periphery of the safe zone 24, which can be considered to be a virtual conduit through which the functional element 94 of the instrument 16 can pass without causing injury to the patient 26.

Figure 7:
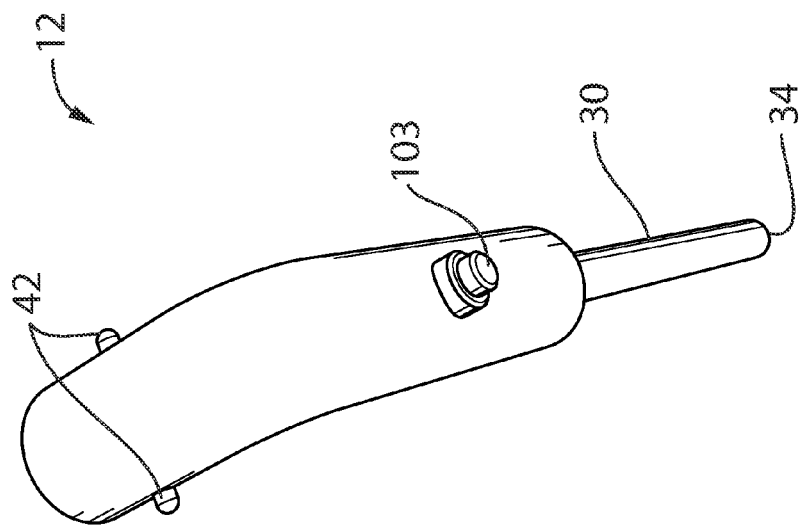
FIG. 7 is an alternative probe for use with the system shown in FIG. 1.

In addition to determining points 58 based on the positions of the sensors 19, the probe 12 may be used to determine some points 58 that are not based on the sensors 19. For example, the probe 12 may be positioned with the aid of the laparoscope 14 so that the probing portion 34 contacts the tip of a bone. When in contact with the bone, the user may indicate to the controller 20 to determine the position of the probing portion 34. For example, the probe 12 may include a button 103 as shown in FIG. 7, which the user can press to indicate to the controller 20 to determine the position of the probing portion 34.

Once the points 58 have been determined, they may be stored in a database as shown at step 221. After the positions of the points 58 have been determined, the probe 12 may be removed from the patient 26.

The surgical instrument 16 is then used on the patient to carry out some task, such as cutting, cauterizing or some other suitable task. During use of the surgical instrument 16, it is possible that the internal organs of the patient may move. If the internal body portions 36 move during surgery it is important that the determined safe zone 24 be updated so as to continue to be useful in preventing inadvertent injury to the patient 26. In order to provide this capability, the sensor 19 associated with each point 58 is capable of sensing self-movement, and indicates to the controller 20 the amount of movement it has incurred in three dimensions. By having the sensors 19 indicate their movement to the controller 20, the controller 20 can update the positions of the associated safe zone defining points 58 relating to the moved sensors 19 and can update the surfaces 60 that define the safe zone 24. In this way, the safe zone 24 can be updated continuously so that the functional element 94 is prevented from injuring the patient 26 even if the internal body portions 36 of the patient 26 move after the safe zone 24 has been initially determined. This is represented as step 222 in FIG. 8b. At step 223, the updated points are also stored in the database.

Any points 58 that were determined without the use of associated sensors 19 cannot be updated as described above, since there are no associated sensors 19 to sense movement of the point 58. Instead, these points 58 may be considered by the controller 20 to be fixed (ie. non-moving during the course of the medical procedure). Preferably any such points are points that are not expected to move during the medical procedure, such as points on certain bones.

During use of the surgical instrument 16, the camera system 22 receives images of the instrument marker 96 and sends the images (which may be referred to as instrument marker input) to the controller 20 (step 224). The controller 20 processes the input using a similar algorithm to that used for determining the position of the probing portion 34, to determine the position of the functional element 94 (step 226). This information is used to determine whether the functional element 94 is within the safe zone 24 (step 228). If the functional element 94 is outside the safe zone 24 (ie. the answer to check step 228 is 'no'), the controller 20 is programmed to carry out at least one action selected from the group of actions consisting of: notifying the user of the surgical instrument 16 that the functional element 94 is outside the safe zone 24; and disabling the functional element 94 (step 230).

Disabling the functional element 94 may be carried out in a number of ways depending on what makes up the functional element 94. For example, if the functional element 94 is a heating element, power may be cut to it. Alternatively, if the functional element 94 includes a sharp edge (eg. a cutting blade), the instrument 16 may include a sheath, and may be configured to automatically cover the functional element 94 with the sheath.

The controller 20 may notify the user in any suitable way that the functional element 94 is outside the safe zone 24. For example, the controller 20 may be configured to generate a selected sound via a speaker, and/or may be configured to generate a selected image on the display 17.

If the functional element 94 is within the safe zone 24 (ie. the answer at check step 228 is 'yes'), the controller 20 sends program control to step 232, wherein it checks if the medical procedure has been completed. This may be indicated by the user pressing a power button or some other control to let the system know to stop. If the procedure is over (ie. the answer to check step 232 is 'yes'), then the program (and thus the method) ends. If the answer to the check step 232 is 'no', then the controller 20 continues to check and update the safe zone 24 as mentioned above at step 222 and to continue to receive instrument marker input at step 224.

The controller 20 may be programmed to divide the safe zone 24 (FIG. 2e) into two or more sub-zones. For example, the safe zone 24 may be divided into a safest zone 98 and a danger zone 100. The safest zone 98 is a central portion of the safe zone 24. If the functional element 94 is kept within the safest zone 98 there is a reduced risk that the user will accidentally move the instrument 16 in such a way as to cause the functional element 94 to contact and cause injury to an internal body portion 36. The danger zone 100 is a peripheral portion of the safe zone 24. In other words it is the portion of the safe zone 24 immediately inwardly adjacent to the virtual surfaces 60 that define the periphery of the safe zone 24. With the safe zone 24 thus divided into multiple sub-zones, the controller 20 may be configured to notify the user via sound and/or images on the display 17 whether the functional element 94 is in a relatively safer part of the safe zone 24 (eg. the safest zone 98) or is in a relatively less safe part of the safe zone 24 (eg. the danger zone 100). For example, a green bar may be displayed on the display 17 when the functional element 94 is within the safest zone 98, a yellow bar may be displayed on the display 17 when the functional element 94 is within the danger zone 100, and a red bar may be displayed when the functional element 94 is outside of the safe zone 24. In another embodiment, the controller 20 may be programmed to give the user a continuously changing indication of the distance of the functional element 94 from the periphery of the safe zone 24, via sound and/or images. For example, the controller 20 may be programmed to emit sound elements (eg. beeps) at a selected frequency of emissions (eg. 2 beeps per second) if the functional element 94 is relatively far from the periphery of the safe zone 24. If the functional element 94 moves closer to the periphery of the safe zone 24, the frequency of the beeps may gradually increase (eg. up to, for example, 5 beeps per second). If the element 94 leaves the safe zone 24, the sound may become continuous.

After the surgical procedure is completed, the instrument 16, the laparoscope 14 and the netting 18 may be removed from the patient 26.

It will be understood that, while it is convenient to have the sensors 19 on the netting 18, it is alternatively possible for at least some of the sensors 19 to be provided without netting 18. These sensors 19 could be inserted individually through an aperture 32 an applied directly to an internal body portion 36 using, for example, a mild adhesive. It will also be understood that the netting 18 may be provided without sensors 19 on it. The netting 18 in such an instance can still be useful to assist in restraining internal body portions from obstructing the surgical instrument 16.

The controller 20 may be configured to record the movements of the surgical instrument and the data relating to the safe zone 24 (ie. the positions of the safe zone defining points 58 throughout the medical procedure). The recording may be made a printed recording, or in a more preferred embodiment, the recording may be made as data written to a database stored on a computer readable medium, such as a flash memory so that the surgical procedure can be played back and reviewed. Instead of a database, the data could be stored in some other computer readable format such as a data file containing a simple list. The capability to play back and review the movements of the instrument and the safe zone in a medical procedure can be useful to for a variety of purposes. For example, the procedure can be reviewed and explained to students in order to train them in the safe carrying out of such a procedure. Also, in the event that there is a complication during the recovery of the patient, the procedure can be reviewed to ensure that there was no injury that occurred that is the source of the complication.

The recording of the data and the movements of the instrument can be provided in any suitable format, such as, for example, audio, graphs, 2D graphic, and 3D graphic, or some combination thereof.

Throughout this disclosure, the components, such as the cameras, the laparoscope, the safe zone definition sensors and the probe have been shown and described as communicating with the controller via suitable electrical conduits such as wires. It will be understood that it is alternatively possible for any of these components to communicate with the controller via wireless means, such as a Bluetooth® connection.

It has been disclosed that the instrument marker 96 and the probe marker 42 be used to identify the instrument 16 and the probe 12 to the controller 20, (ie. to distinguish each from each other and from any other components sensed by the controller 20). However, an element that is separate from the marker 42 or 96 could alternatively be provided on the instrument 16 and the probe 12 respectively to identify each to the controller 20. For example, a unique RFID tag can be provided on each to identify each to the controller 20.

While the above description constitutes a plurality of embodiments of the present invention, it will be appreciated that the present invention is susceptible to further modification and change without departing from the fair meaning of the accompanying claims.

The invention claimed is:

1. A surgical system for use on a body of a patient, comprising:
   a probe including an interior portion that is configured to be at least partially inserted into the body of the patient during use, a probe body to which the interior portion of the probe is connected, wherein the probe body is configured to be outside the body of the patient during use, wherein the interior portion of the probe includes a probing portion, and a probe marker on the probe body;
   a surgical instrument including an interior portion that is configured to be at least partially inserted into the body of the patient during use, an instrument body to which the interior portion of the surgical instrument is connected, wherein the instrument body is configured to be outside the body of the patient during use, wherein the interior portion of the surgical instrument includes a functional element, and an instrument marker on the instrument body;
   a laparoscope including an interior portion that is configured to be at least partially inserted into the body of the patient during use, a laparoscope body to which the interior portion of the laparoscope is connected, wherein the laparoscope body is configured to be outside the body of the patient during use, wherein the interior portion of the laparoscope includes an image receiving element, wherein, during use, the image receiving element is positionable in a surgical field in the body of the patient to receive images of the probing portion when the probing portion is in the surgical field and to receive images of the functional element when the functional element is in the surgical field;
   a display configured to display the images of the probing portion and of the functional element received by the laparoscope;
   a tracking system that includes at least one tracking system sensor positionable to track the probe marker during use of the surgical probe and to track the instrument marker during use of the surgical instrument;

netting that is insertable into the body of the patient and is positionable to restrain at least some of the internal body portions of the patient from obstructing the surgical instrument, a plurality of safe zone definition sensors positioned on the netting, wherein, for each safe zone definition sensor, the safe zone definition sensor is configured to detect when the probing portion is at a selected proximity to the safe zone definition sensor; and a controller, wherein for each safe zone definition sensor, the controller is programmed to:

(a) receive an indication from the safe zone definition sensor when the probing portion is at the selected proximity to the safe zone definition sensor;

(b) receive probe marker input from the tracking system corresponding to a position of the probe marker when having received the indication from step (a); and (c) determine the position of the safe zone definition sensor based on the probe marker input;

and wherein the controller is further programmed to:

(d) determine safe zone defining positions which define a safe zone within which the surgical instrument can operate without causing injury to the patient based at least in part on the plurality of positions determined at step (c);

(e) receive substantially continuous instrument marker input from the tracking system corresponding to a current position of the instrument marker which in turn corresponds to a current position of the functional element;

(f) determine substantially continuously the current position of the functional element based on the instrument marker input;

(g) determine substantially continuously whether the functional element is within the safe zone based on the current position of the functional element determined in step (f); and (h) carry out at least one action if the controller determines in step (g) that the functional element is outside of the safe zone, wherein the at least one action is selected from the group of actions consisting of: notifying a user of the surgical instrument that the functional element is outside the safe zone; and disabling the functional element.

2. A surgical system as claimed in claim 1, wherein, for each safe zone definition sensor, the safe zone definition sensor is configured to detect when the probing portion is in contact with the safe zone definition sensor.

3. A surgical system as claimed in claim 1, wherein the controller is further programmed in step (h) to carry out both actions selected from the group of actions consisting of: notifying a user of the surgical instrument that the surgical instrument is outside the safe zone; and disabling the functional element.

4. A surgical system as claimed in claim 1,
wherein the controller is further programmed to:
(i) determine whether the functional element is within a danger zone, wherein the danger zone is a peripheral portion of the safe zone, and
(j) notify the user of the surgical instrument that the functional element is in the danger zone, if the functional element is determined to be in the danger zone in step (i).

5. A surgical system as claimed in claim 1, wherein the controller is programmed to record a history of positions of the functional element determined at step (f) during a surgical procedure.

6. A surgical system as claimed in claim 1, wherein the controller is programmed to record in a computer readable format on a computer readable medium a history of positions of the functional element determined at step (f) during a surgical procedure.

7. A surgical system as claimed in claim 1, wherein the functional element includes at least one sharp edge and at least one sheath, and wherein the action of disabling the functional element includes covering the at least one sharp edge with the at least one sheath.

8. A surgical system as claimed in claim 1, wherein each safe zone definition sensor is configured to sense self-movement in three dimensions and is further configured to indicate to the controller the amount of self-movement that takes place, and wherein, upon receiving an indication of self-movement from at least one of the safe zone definition sensors, the controller is further programmed to update the safe zone defining positions based on the indication.

9. A surgical system as claimed in claim 8, wherein the controller is programmed to record in a computer readable format on a computer readable medium a history of positions of the functional element determined at step (f) during a surgical procedure and a history of the safe zone defining positions during a surgical procedure.

10. A surgical system as claimed in claim 8, wherein each safe zone definition sensor includes an accelerometer.

11. A surgical system as claimed in claim 1, wherein the netting includes a plurality of hold-down elements which are attachable to points outside of the body of the patient to hold the netting in such a way as to restrain at least some of the internal body portions of the patient from obstructing the surgical instrument.

12. A surgical system as claimed in claim 1, wherein the functional element is selected from the group of functional elements consisting of: a cutting blade and a heated element.

13. A surgical system as claimed in claim 1, wherein the tracking system includes at least one tracking system camera positioned to receive images of the probe marker when the probe is being used on the patient and wherein the controller is programmed to determine the position of the probe based on the images of the probe marker and positioned to receive images of the instrument marker when the instrument is being used on the patient and wherein the controller is programmed to determine the position of the instrument based on the images of the instrument marker.

14. A surgical system as claimed in claim 13, wherein at least one of the probe marker and the instrument marker includes a plurality of LEDs.

15. A surgical system as claimed in claim 14, wherein at least one of the probe marker and the instrument marker includes a plurality of LEDs that are configured to emit infrared light.

16. A surgical system as claimed in claim 13, wherein at least one of the probe marker and the instrument marker includes an image of a polygon and a plurality of LEDs.

17. A surgical system as claimed in claim 1, wherein the action of notifying a user of the surgical instrument that the functional element is outside the safe zone comprises an emission of an audible sound.

18. A surgical system as claimed in claim 1, wherein the controller is programmed to emit and alter an audible sound as the functional element approaches a periphery of the safe zone so as to provide to the user of the surgical instrument an indication of the proximity of the functional element to the periphery of the safe zone.

19. A surgical system as claimed in claim 1, wherein the controller is programmed to emit an audible sound made up of a plurality of sound elements emitted at a frequency, wherein, as the functional element approaches a periphery of the safe zone the controller is programmed to alter the frequency of the sound elements emitted so as to provide to the user of the surgical instrument an indication of the proximity of the functional element to the periphery of the safe zone.

20. A surgical system as claimed in claim 1, wherein the tracking system includes at least one tracking system camera positioned to receive images of the probe marker and wherein the controller is programmed to determine the position of the probe based on the images of the probe marker.

21. A method of using a surgical system on a body of a patient, comprising:
(a) providing a probe including an interior portion that is configured to be at least partially inserted into the body of the patient during use, a probe body to which the interior portion of the probe is connected, wherein the probe body is configured to be outside the body of the patient during use, wherein the interior portion of the probe includes a probing portion;
(b) providing a surgical instrument including an interior portion that is configured to be at least partially inserted into the body of the patient during use, an instrument body to which the interior portion of the surgical instrument is connected, wherein the instrument body is configured to be outside the body of the patient during use, wherein the interior portion of the surgical instrument includes a functional element;
(c) providing a laparoscope including an interior portion that is configured to be at least partially inserted into the body of the patient during use, a laparoscope body to which the interior portion of the laparoscope is connected, wherein the laparoscope body is configured to be outside the body of the patient during use, wherein the interior portion of the laparoscope includes an image receiving element, wherein, during use, the image receiving element is positionable in a surgical field in the body of the patient to receive images of the probing portion when the probing portion is in the surgical field and to receive images of the functional element when the functional element is in the surgical field;
(d) providing netting that is insertable into the body of the patient and is positionable to restrain at least some of the internal body portions of the patient from obstructing the surgical instrument;
(e) providing a plurality of safe zone definition sensors positioned on the netting, wherein, for each safe zone definition sensor, the safe zone definition sensor is configured to detect when the probing portion is at a selected proximity to the safe zone definition sensor;
wherein, for each safe zone definition sensor, the method further comprises:
(f) receive an indication from the safe zone definition sensor when the probing portion is at the selected proximity to the safe zone definition sensor;\
(g) determine the position of the probe when an indication is received in step (f);
(h) determine, the position of the safe zone definition sensor based on position of the probe determined in step (g);
wherein the method further comprises:
(i) determine safe zone defining positions which define a safe zone within which the surgical instrument can operate without causing injury to the patient based at least in part on the plurality of positions determined at step (h);
(j) determine substantially continuously whether the functional element is within the safe zone; and (k) carry out at least one action if the controller determines in step (j) that the functional element is outside of the safe zone, wherein the at least one action is selected from the group of actions consisting of: notifying a user of the surgical instrument that the functional element is outside the safe zone; and disabling the functional element.

22. A method as claimed in claim 21, wherein:
the probe includes a probe marker on the probe body;
the instrument includes an instrument marker on the instrument body; and
wherein the method further comprises:
(l) providing a tracking system that includes at least one tracking system sensor positionable to track the probe marker during use of the surgical probe and to track the instrument marker during use of the surgical instrument;
wherein step (g) includes:
(m) receiving, for each indication received in step (f), probe marker input from the tracking system corresponding to a position of the probe marker when having received the indication from step (f), and determining the position of the probe based on the probe marker input;
and wherein step (h) includes:
(n) determining the position of each safe zone definition sensor based on the probe marker input;
and wherein step (j) includes:
(o) receiving substantially continuous instrument marker input from the tracking system corresponding to a current position of the instrument marker which in turn corresponds to a current position of the functional element;
(p) determining substantially continuously the current position of the functional element based on the instrument marker input; and
(q) determining substantially continuously whether the functional element is within the safe zone based on the current position of the functional element determined in step (p).

23. A method as claimed in claim 22, further comprising recording in a computer readable format on a computer readable medium a history of positions of the functional element determined at step (p) during a surgical procedure.

24. A method as claimed in claim 21, wherein, for each safe zone definition sensor, the safe zone definition sensor is configured to detect when the probing portion is in contact with the safe zone definition sensor.

25. A method as claimed in claim 21, further comprising:
(r) determining whether the functional element is within a danger zone, wherein the danger zone is a peripheral portion of the safe zone, and (s) notifying the user of the surgical instrument that the functional element is in the danger zone, if the functional element is determined to be in the danger zone in step (r).

26. A method as claimed in claim 21, wherein each safe zone definition sensor is configured to sense self-movement in three dimensions and is further configured to indicate the amount of self-movement that takes place, and wherein the method further comprises: updating the safe zone defining positions based on the indication upon receiving an indication of self-movement from at least one of the safe zone definition sensors.

27. A method as claimed in claim 26, further comprising recording in a computer readable format on a computer readable medium a history of positions of the functional element determined at step (p) during a surgical procedure and a history of the safe zone defining positions during a surgical procedure.

28. A method as claimed in claim 26, wherein each safe zone definition sensor includes an accelerometer.

29. A method as claimed in claim 21, wherein the netting includes a plurality of hold-down elements which are attachable to points outside of the body of the patient to hold the netting in such a way as to restrain at least some of the internal body portions of the patient from obstructing the surgical instrument.

30. A method as claimed in claim 21, wherein the functional element is selected from the group of functional elements consisting of: a cutting blade and a heated element.

* * * * *